US00PP26778P2

(12) United States Plant Patent
Dummen

(10) Patent No.: US PP26,778 P2
(45) Date of Patent: May 31, 2016

(54) **NEW GUINEA *IMPATIENS* PLANT NAMED 'DUEMAGLASP'**

(50) Latin Name: *Impatiens hawkeri*
Varietal Denomination: Duemaglasp

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 96 days.

(21) Appl. No.: 14/120,877

(22) Filed: Jul. 7, 2014

(51) Int. Cl.
*A01H 5/02* (2006.01)

(52) U.S. Cl.
USPC ..... Plt./318.1

(58) Field of Classification Search
USPC ..... Plt./318.1
See application file for complete search history.

*Primary Examiner* — Susan McCormick Ewoldt
(74) *Attorney, Agent, or Firm* — C. A. Whealy

(57) ABSTRACT

A new and distinct cultivar of *Impatiens* plant named 'Duemaglasp' characterized by its upright, outwardly spreading and mounding plant habit; freely branching habit; vigorous growth habit; dark green-colored leaves; freely and early flowering habit; large dark and light red purple bi-colored flowers; and good garden performance.

1 Drawing Sheet

Botanical designation: *Impatiens hawkeri*.
Cultivar denomination: 'DUEMAGLASP'.

BACKGROUND OF THE INVENTION

The present invention relates to a new and distinct cultivar of New Guinea *Impatiens* plant, botanically known as *Impatiens hawkeri* and hereinafter referred to by the name 'Duemaglasp'.

The new *Impatiens* plant is a product of a planned breeding program conducted by the Inventor in Rheinberg, Germany. The objective of the breeding program is to create new vigorous and uniform New Guinea *Impatiens* plants with large attractive flowers.

The new *Impatiens* plant originated from a cross-pollination made by the Inventor in July, 2009 in Rheinberg, Germany of a proprietary selection of *Impatiens hawkeri* identified as code number F-0313-012, not patented, as the female, or seed, parent with a proprietary selection of *Impatiens hawkeri* identified as code number F-015-001, not patented, as the male, or pollen, parent. The new *Impatiens* plant was discovered and selected by the Inventor as a single flowering plant from within the progeny of the stated cross-pollination in a controlled greenhouse environment in Rheinberg, Germany in May, 2013.

Asexual reproduction of the new *Impatiens* plant by terminal cuttings in a controlled greenhouse environment in Rheinberg, Germany since June, 2013 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Duemaglasp'. These characteristics in combination distinguish 'Duemaglasp' as a new and distinct *Impatiens* plant:

1. Upright, outwardly spreading and mounding plant habit.
2. Vigorous growth habit.
3. Freely branching habit.
4. Dark green-colored leaves.
5. Freely and early flowering habit.
6. Large light and dark red purple bi-colored flowers.
7. Good garden performance.

Plants of the new *Impatiens* can be compared to plants of the female parent selection. Plants of the new *Impatiens* differ primarily from plants of the female parent selection in flower color as plants of the female parent selection have lavender-colored flowers. In addition, plants of the new *Impatiens* are more vigorous and have larger flowers than plants of the female parent selection.

Plants of the new *Impatiens* can be compared to plants of the male parent selection. Plants of the new *Impatiens* differ primarily from plants of the male parent selection in flower color as plants of the male parent selection have light and dark purple bi-colored flowers.

Plants of the new *Impatiens* can be compared to plants of *Impatiens hawkeri* 'Kimpgua', disclosed in U.S. Plant Pat. No. 10,429. In side-by-side comparisons conducted in Rheinberg, Germany, plants of the new *Impatiens* differed primarily from plants of 'Kimpgua' in the following characteristics:

1. Plants of the new *Impatiens* were larger than plants of 'Kimpgua'.
2. Plants of the new *Impatiens* were more vigorous than plants of 'Kimpgua'.
3. Plants of the new *Impatiens* had larger leaves than plants of 'Kimpgua'.
4. Plants of the new *Impatiens* had larger flowers than plants of 'Kimpgua'.

BRIEF DESCRIPTION OF THE PHOTOGRAPH

The accompanying colored photograph illustrates the overall appearance of the new *Impatiens* plant showing the colors as true as it is reasonably possible to obtain in colored reproductions of this type. Colors in the photograph may differ slightly from the color values cited in the detailed botanical description which accurately describe the colors of the new *Impatiens* plant.

The photograph comprises a side perspective view of a typical flowering plant of 'Duemaglasp' grown in a container.

DETAILED BOTANICAL DESCRIPTION

The aforementioned photograph and following observations, measurements and values describe plants grown during the summer in 10.5-cm containers in a glass-covered greenhouse in Rheinberg, Germany and under cultural practices typical of commercial New Guinea *Impatiens* production. During the production of the plants, night temperatures averaged 18° C. and light levels averaged 4,500 lux. Plants were pinched one time three weeks after planting and were 16 weeks old when the photograph and description were taken. In the following description, color references are made to The Royal Horticultural Society Colour Chart, 2007 Edition, except where general terms of ordinary dictionary significance are used.

Botanical classification: *Impatiens hawkeri* 'Duemaglasp'.

Parentage:

*Female, or seed, parent.*—Proprietary selection of *Impatiens hawkeri* identified as code number F-0313-012, not patented.

*Male, or pollen, parent.*—Proprietary selection of *Impatiens hawkeri* identified as code number F-015-001, not patented.

Propagation:

*Type.*—By terminal cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; white in color.

*Rooting habit.*—Freely branching; dense.

Plant description:

*Plant and growth habit.*—Upright to outwardly spreading and mounding plant habit; freely branching habit with about 17 lateral branches developing per plant; vigorous growth habit.

*Plant height.*—About 33 cm.

*Plant diameter.*—About 60 cm.

Lateral branch description:

*Length.*—About 20 cm.

*Diameter.*—About 8 mm.

*Internode length.*—About 2.9 cm.

*Strength.*—Strong.

*Aspect.*—Initially upright to outwardly spreading.

*Texture.*—Smooth, glabrous.

*Color.*—Close to 59A.

Leaf description:

*Arrangement.*—Opposite or in whorls; simple.

*Length.*—About 9.8 cm.

*Width.*—About 3 cm.

*Shape.*—Ovate.

*Apex.*—Apiculate.

*Base.*—Obtuse.

*Margin.*—Serrulate with ciliation.

*Texture, upper and lower surfaces.*—Smooth, glabrous; leathery.

*Venation pattern.*—Pinnate; arcuate.

*Color.*—Developing leaves, upper surface: Close to 146A. Developing leaves, lower surface: Close to 60A. Fully expanded leaves, upper surface: Close to 147A; venation, close to 58A. Fully expanded leaves, lower surface: Close to 60B; venation, close to 60B.

*Petiole length.*—About 2 cm.

*Petiole diameter.*—About 2.8 mm.

*Petiole texture, upper and lower surfaces.*—Smooth, glabrous; leathery.

*Petiole color, upper surface.*—Close to 61B.

*Petiole color, lower surface.*—Close to 60B.

Flower description:

*Flower type and flowering habit.*—Single rounded and flat axillary flowers; freely flowering habit, typically about five open flowers and flower buds per lateral branch; flowers positioned above and beyond the foliar plane, flowers typically face mostly upright to outwardly.

*Flower longevity.*—Flowers typically last about one to two days on the plant under greenhouse conditions; petals self-cleaning, gynoecium persistent.

*Fragrance.*—None detected.

*Natural flowering season.*—Year-round under greenhouse conditions; in the garden, flowering from spring until fall in Germany; early flowering habit, plants typically begin flowering about eight weeks after planting.

*Flower buds.*—Length: About 1.4 cm. Diameter: About 1 cm. Shape: Ovate. Color: Close to 59B.

*Flower diameter.*—About 7 cm.

*Flower depth.*—About 2.5 cm.

*Petals.*—Quantity and arrangement: Five per flower in a single whorl. Length: About 3.3 cm. Width: About 3.8 cm. Shape: Obcordate. Apex: Cordate; rounded. Base: Acute. Margin: Entire. Texture, upper and lower surfaces: Smooth, glabrous; satiny. Color: When opening and fully opened, upper surface: Close to 74D and 74A; colors becoming closer to 59B with development. When opening and fully opened, lower surface: Close to 57D and 66A; color does not change with development.

*Sepals.*—Quantity and arrangement: Three in a single whorl; one modified into an elongated spur. Length: About 1.9 cm. Width: About 6 mm. Shape: Lanceolate. Apex: Apiculate. Base: Acute. Margin: Entire. Texture, upper and lower surfaces: Smooth, glabrous. Color, upper and lower surfaces: Close to 34B to 34C. Spur length: About 4.3 cm. Spur diameter: At the flower, about 3 mm; towards the apex, about 1 mm. Spur texture: Smooth, glabrous. Spur color: Close to 57B.

*Peduncles.*—Length: About 5.5 cm. Diameter: About 2 mm to 3 mm. Angle: Upright to outward. Strength: Moderately strong; flexible. Texture: Smooth, glabrous. Color: Close to 60A.

*Reproductive organs.*—Stamens: Quantity: Five fused at anthers; filaments free. Filament length: About 2 mm. Filament color: Close to 1D. Anther length: About 5 mm. Anther shape: Oval. Anther color: Close to 59A. Pollen amount: Abundant. Pollen color: Close to 11D. Pistils: Quantity per flower: One. Pistil length: About 7 mm. Stigma shape: Crested. Stigma color: Close to 46B. Style length: About 2 mm. Style color: Close to 46B. Ovary color: Close to 150C.

*Seeds and fruits.*—Seed and fruit production has not been observed on plants of the new *Impatiens*.

Disease & pest resistance: Plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Duemaglasp' as illustrated and described.

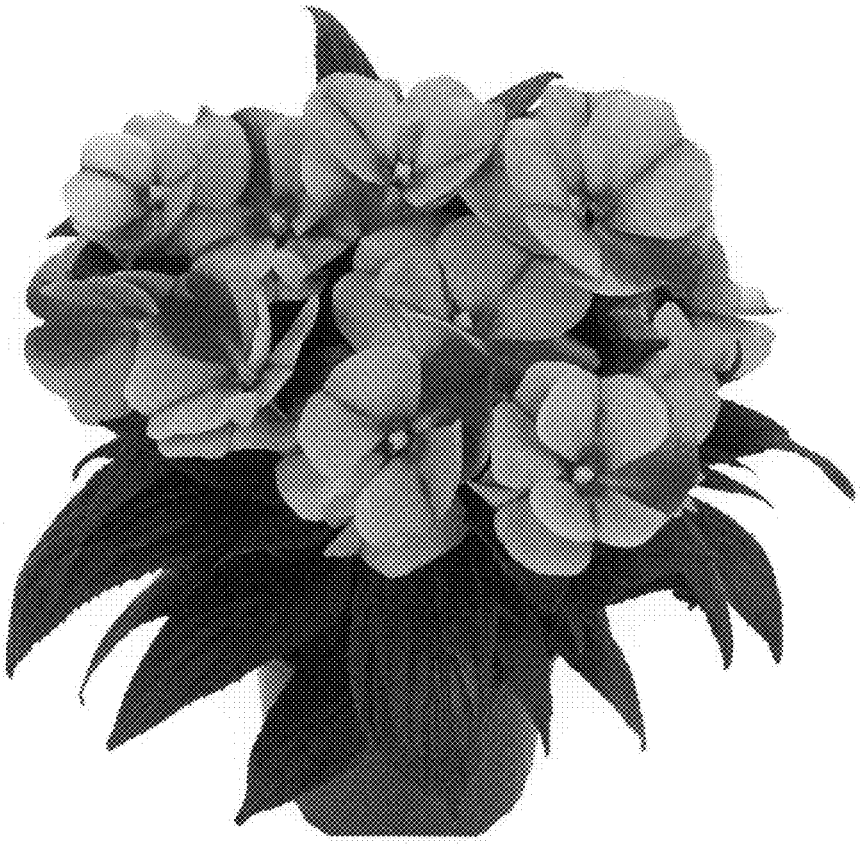

* * * * *